(12) United States Patent
Shen et al.

(10) Patent No.: US 6,663,854 B1
(45) Date of Patent: Dec. 16, 2003

(54) ALUMINUM-ZIRCONIUM ANTIPERSPIRANT SALTS MADE WITH ZIRCONIUM SALTS HAVING LOW ZR:CL RATIO

(76) Inventors: Yan-Fei Shen, 2 Staiti Cir., Canton, MA (US) 02021; Richard Oryszczak, 330 S. Clyde Ct., Palatine, IL (US) 60067; Angel L. Carrillo, 11 Vane St., Wellesley, MA (US) 02482

( * ) Notice: Subject to any disclaimer, the term of this patent is extended or adjusted under 35 U.S.C. 154(b) by 6 days.

(21) Appl. No.: 10/175,250

(22) Filed: Jun. 19, 2002

(51) Int. Cl.$^7$ .............. A61K 7/32; A61K 7/34; A61K 7/38; A61K 7/00
(52) U.S. Cl. .............. 424/65; 424/66; 424/68; 424/400; 424/401
(58) Field of Search .............. 424/65, 66, 68, 424/400, 401

(56) References Cited

U.S. PATENT DOCUMENTS

| | | | |
|---|---|---|---|
| 2,814,585 A | 11/1957 | Daley | 167/90 |
| 2,854,382 A | 9/1958 | Grad | 167/90 |
| 4,331,609 A | 5/1982 | Orr | 424/66 |
| 4,435,382 A | * 3/1984 | Shin et al. | 424/66 |
| 4,775,528 A | 10/1988 | Callaghan et al. | 424/66 |
| 4,871,525 A | 10/1989 | Giovanniello et al. | 424/66 |
| 4,900,534 A | 2/1990 | Inward | 424/66 |
| 5,225,187 A | 7/1993 | Carmody | 424/66 |
| 5,296,623 A | 3/1994 | Katsoulis et al. | 424/66 |
| 5,330,751 A | 7/1994 | Curtin | 424/66 |
| 5,718,876 A | 2/1998 | Parekh | 424/65 |
| 5,955,064 A | 9/1999 | Giovanniello | 424/65 |
| 6,066,314 A | 5/2000 | Tang | 424/65 |
| 6,126,928 A | 10/2000 | Swaile | 424/65 |
| 6,375,937 B1 | 4/2002 | Chopra | 424/65 |

FOREIGN PATENT DOCUMENTS

| | | |
|---|---|---|
| CA | 1153313 | 9/1983 |
| EP | 653203 | 5/1995 |
| GB | 1353916 | 5/1974 |
| WO | 01/56539 | 8/2001 |
| WO | 02/34223 | 5/2002 |

OTHER PUBLICATIONS

Bretschneider et al, "Antiperspirant Efficacy", Proceedings of the 9$^{th}$ IFSCC Congress, Boston, MA 1976, pp. 263–75.
Bretschneider et al, "Physical Properties of Antiperspirantsas Related to Their Efficacy", reprint of article from *Cosmetics and Perfumery*, Feb. 1975.

* cited by examiner

Primary Examiner—Shelley A. Dodson
(74) Attorney, Agent, or Firm—Stephen P. Williams

(57) ABSTRACT

Disclosed are enhanced efficacy aluminum-zirconium chlorohydrate antiperspirant salts having a metal (Al+Zr) to chloride ratio of about 0.9 to about 1.2, preferably about 0.9 to about 1.1, most preferably about 0.9 to about 1.0. To achieve the highest possible antiperspirant efficacy, these salts are made with or include a zirconium hydroxychloride of the formula $Zr(OH)_{4-b}Cl_b$, wherein b is about 2.8 to about 4.0, preferably about 3.2 to about 4.0, so that the Zr:Cl ratio in said zirconium hydroxychloride is about 0.36 to about 0.25, preferably about 0.31 to about 0.25. The present invention also embraces methods of making such antiperspirant salts and aqueous solutions of such antiperspirant salts. The present invention further embraces topical compositions comprising a dermatologically acceptable carrier and a perspiration reducing effective amount of an aluminum-zirconium antiperspirant salt as described above.

26 Claims, No Drawings

ALUMINUM-ZIRCONIUM ANTIPERSPIRANT SALTS MADE WITH ZIRCONIUM SALTS HAVING LOW ZR:CL RATIO

BACKGROUND OF THE INVENTION

The present invention relates to aluminum-zirconium antiperspirant salts made with zirconium salts having a low Zr:Cl ratio. The present invention also embraces methods of making these antiperspirant salts and compositions containing these antiperspirant salts.

Aluminum-zirconium antiperspirant salts have been known for several decades. See, for example, U.S. Pat. No. 2,814,585 (Daley), U.S. Pat. No. 2,854,382 (Grad), GB 1,353,916 (Bolich), U.S. Pat. No. 4,331,609 (Orr), U.S. Pat. No. 4,775,528 (Callaghan), U.S. Pat. No. 4,871,525 (Giovanniello), U.S. Pat. No. 4,900,534 (Inward), U.S. Pat. No. 5,225,187 (Carmody), U.S. Pat. No. 5,296,623 (Katsoulis), U.S. Pat. No. 5,330,751 (Curtin), EP 653,203 (Rosenberg), U.S. Pat. No. 5,718,876 (Parekh) and U.S. Pat. No. 5,955,064 (Giovanniello). Some of these aluminum-zirconium antiperspirant salts are described as having enhanced efficacy, which means that they provide greater sweat reduction than conventional antiperspirant salts. EP 653,203 (Rosenberg) suggests that such salts are improved by maintaining the molecular weight of the zirconium species as low as possible.

Prior to the discovery of the enhanced Al—Zr salts, U.S. Pat. No. 4,331,609 suggested that Al—Zr salts with a metal to chloride ratio below about 1.3 (e.g., 1.25) may be more efficacious than salts with a higher metal to chloride ratio. In U.S. Pat. No. 6,126,928 there are described certain polyhydric alcohol solutions of the salts described in the aforementioned '609 patent. More recently, U.S. Pat. No. 6,375,937 described aluminum-zirconium tetrachlorohydrex glycine salts having a metal to chloride ratio in the range of 0.9 to 1.2 and a glycine to zirconium ratio greater than 1.3. None of these disclosures suggest that any advantage is obtained through the use of a particular zirconium species.

SUMMARY OF THE INVENTION

The present invention embraces enhanced efficacy aluminum-zirconium chlorohydrate antiperspirant salts having a metal (Al+Zr) to chloride ratio of about 0.9 to about 1.2, preferably about 0.9 to about 1.1, most preferably about 0.9 to about 1.0. To achieve the highest possible antiperspirant efficacy, these salts are made with or include a zirconium hydroxychloride of the formula $Zr(OH)_{4-b}Cl_b$ wherein b is about 2.8 to about 4.0, preferably about 3.2 to about 4.0, so that the Zr:Cl ratio in said zirconium hydroxychloride is about 0.36 to about 0.25, preferably about 0.31 to about 0.25. The present invention also embraces methods of making such antiperspirant salts and aqueous solutions of such antiperspirant salts. The present invention further embraces topical compositions comprising a dermatologically acceptable carrier and a perspiration reducing effective amount of an aluminum-zirconium antiperspirant salt as described above.

DETAILED DESCRIPTION OF THE INVENTION

The present invention embraces enhanced efficacy aluminum-zirconium chlorohydrate antiperspirant salts having a metal (Al+Zr) to chloride ratio of about 0.9 to about 1.2, preferably about 0.9 to about 1.1, most preferably about 0.9 to about 1.0. The Al—Zr salts generally have the empirical formula $Al_nZr(OH)_{[3n+4-m(n+1)]}(Cl)_{[m(n+1)]}$ where n is 2.0 to 10.0, preferably 3.0 to 8.0, and m is about 0.83 to about 1.11 (which corresponds to M:Cl≅1.2–0.9), preferably about 0.90 to about 1.11 (which corresponds to M:Cl≅1.1–0.9), and more preferably about 1.00 to about 1.11 (which corresponds to M:Cl≅1.0–0.9). These salts also will typically include an amino acid such as glycine, alanine, valine, serine, leucine, or aminobutyric acid, preferably glycine, generally in an amount to provide an amino acid to zirconium ratio (e.g., Gly:Zr) of about 0.8 to about 4.0, preferably about 1.0 to about 2.0. These salts also generally have some water of hydration associated with them, typically on the order of 1 to 5 moles per mole of salt (typically, about 1% to about 16%, more typically about 4% to about 13% by weight). These salts are generally referred to as aluminum-zirconium tetrachlorohydrates when the Al:Zr ratio is between 2 and 6 and as aluminum-zirconium octachlorohydrates when the Al:Zr ratio is between 6 and 10.

A critical feature of the present invention is that the aluminum-zirconium chlorohydrate salts must be made with or include a zirconium hydroxychloride having a low Zr:Cl ratio. The Zr:Cl ratio preferably will be about 0.25 to about 0.36, more preferably about 0.25 to about 0.31, and most preferably about 0.25 to about 0.29. Preferred zirconium salts are those having the general formula $Zr(OH)_{4-b}Cl_b$ wherein b is about 2.8 to about 4.0 (i.e., Zr:Cl ≅0.36–0.25), more preferably about 3.2 to about 4.0 (i.e., Zr:Cl≅0.31–0.25), most preferably about 3.4 to about 4.0 (Zr:Cl≅0.29–0.25). (It should be noted that when b is 4, the zirconium salt is essentially $ZrCl_4$.) The zirconium salts, when used as a powder, generally have some water of hydration associated with them, typically on the order of 1 to 7 moles per mole of salt. In addition, the zirconium salts will usually include an amino acid, as described above, to prevent gellation in aqueous solution. Zirconium salts with a low Zr:Cl ratio are preferred because such salts appear to have a lower molecular weight than other zirconium salts and appear to maintain the lower molecular weight form even after being combined with the aluminum salt to form the aluminum-zirconium chlorohydrate. It is theorized that the presence of the low molecular weight zirconium species results in higher antiperspirant efficacy in the final Al—Zr salt. In addition, the use of zirconium salts with a low Zr:Cl ratio also facilitates the manufacture of the Al—Zr salt with a low metal:Cl ratio.

The Al—Zr salt compositions of the present invention are manufactured by mixing in an aqueous solution an aluminum antiperspirant salt (preferably an enhanced aluminum antiperspirant salt as described below) and a zirconium hydroxychloride salt (as described above), each salt being present in an amount to provide the desired Al:Zr molar ratio, and including in the aqueous solution sufficient chloride ion to provide the desired metal:chloride (M:Cl) ratio (i.e., about 0.9 to about 1.2, preferably about 0.9 to about 1.1, most preferably about 0.9 to about 1.0). If there is insufficient chloride ion provided by the aluminum and zirconium salts, additional chloride ion may be provided, for example, by addition of an appropriate amount of HCi (or other suitable chloride source such as $AlCl_3$). Typically the mixing of components will take about 0.25 to 5 hours at room temperature (20–25° C.). The aqueous solution of Al—Zr salt may be used or stored as an aqueous solution, or it may be spray dried or vacuum dried to obtain the salt in solid powder form. When the aluminum antiperspirant salt utilized is one with an elevated HPLC peak 4:3 area ratio, then preferably the Al—Zr salt will be dried to a solid while the peak 4:3 area ratio is above 0.4 to obtain a salt with maximum efficacy.

As an alternative to the above-described solution process, it is also possible to dry blend an aluminum antiperspirant salt with the zirconium hydroxychloride, provided that the molar quantities of Al, Zr, and Cl in the starting components that are blended are such as to provide the correct molar ratios of Al:Zr and M:Cl in the final product.

Preferred aluminum salts for use as starting materials are those having the general formula $Al_2(OH)_{6-a}Cl_a$ wherein a is about 0.3 to about 5, preferably about 0.8 to about 2.5, more preferably about 1 to about 2 (such that the Al to Cl mole ratio is about 0.9:1 to about 2.1:1). These salts generally have some water of hydration associated with them, typically on the order of 1 to 6 moles per mole of salt. Most preferably the aluminum salt is aluminum chlorohydrate, especially 5/6 basic aluminum chlorohydrate where a is about 1, such that the aluminum to chlorine mole ratio is about 1.9:1 to 2.1:1, typically about 1.95:1. Aluminum chlorohydrate is referred to as "ACH" herein.

Preferably, the ACH is an enhanced efficacy form, sometimes written as ACH', which has an HPLC peak 4 to peak 3 area ratio of at least 0.5, preferably at least 0.7, with at least 70%, preferably at least 80%, of the aluminum contained in peaks 3 and 4. The enhanced efficacy aluminum chlorohydrates are readily made by heating a dilute ACH solution (e.g., about 10% salt concentration by weight) at about 80–100° C. for about 4 to 20 hours. It has been found that the greatest antiperspirant efficacy in the final Al—Zr antiperspirant salt can be obtained when an enhanced efficacy aluminum antiperspirant salt is used as one of the starting materials. As an alternative to or in conjunction with the above-described aluminum salt, it is also possible to employ aluminum chloride ($AlCl_3$), provided that the molar ratio of the various reactants is adjusted to arrive at the desired molar ratio of the aluminum, zirconium, hydroxyl and chloride moieties in the final Al—Zr salt prepared.

The aluminum-zirconium chlorohydrate salts of the present invention generally have superior antiperspirant efficacy and, surprisingly, maintain the superior antiperspirant efficacy even when stored as an aqueous solution. This is a distinct advantage over previously known enhanced antiperspirant salts, whose efficacy deteriorates in aqueous solution.

The antiperspirant salts of the present invention may be formulated into topical compositions such as liquids (e.g., for roll-on or porous applicators), lotions, creams, gels, soft-solids, solid sticks, etc. Such compositions will comprise the antiperspirant salt in a perspiration reducing effective amount and a dermatologically acceptable carrier.

In particular, aqueous solutions of these antiperspirant salts may be directly utilized in oil-in-water and water-in-oil emulsions, such as the currently popular clear gel formulations, or in other aqueous based compositions such as aqueous based roll-ons. Preferred aqueous liquid compositions will comprise about 8% to about 45% (USP) by weight, preferably about 18% to about 38% (USP) by weight, antiperspirant salt and about 20% to about 90%, preferably about 45% to about 80%, water, such aqueous compositions optionally including other water soluble cosmetic ingredients (e.g., ethanol or polyhydric alcohol). These aqueous solutions may be stored indefinitely without significant loss of efficacy, unlike solutions of conventional enhanced efficacy salts, and may be diluted to an appropriate concentration (e.g., 6%–22% USP) for topical application when formulated into a commercial product.

It is also possible to make a solution of the Al—Zr antiperspirant salt in a liquid polyhydric alcohol such as propylene glycol. The liquid polyhydric alcohol will typically have from three to six carbon atoms and from two to six hydroxyl groups. Such a solution may be readily obtained by adding the polyhydric alcohol to an aqueous solution of the Al—Zr salt as described above, then evaporating off the water under vacuum (see, for example, U.S. Pat No. 5,643,558). Such a polyhydric alcohol composition may advantageously comprise about 8% to about 45% (USP) of said antiperspirant salt. This product can then be readily formulated into topical antiperspirant compositions which use a polyhydric alcohol vehicle, such as clear sticks gelled with dibenzylidene sorbitol or other gellants (see, for example, U.S. Pat. No. 5,705,171).

It is especially preferred to produce the Al—Zr salts of the present invention in solid powder form, for example by spray drying or vacuum drying the aqueous solution in which these salts are produced. The powdered antiperspirant salts may then be formulated into any known type of topical composition which utilizes powdered salts, including, in particular, liquid roll-on, cream, soft-solid and solid stick formulations in which the powdered salt is suspended in an anhydrous, dermatologically acceptable carrier, particularly a carrier comprising a silicone (e.g., cyclomethicone, dimethicone, etc.), typically at a concentration of about 6% to about 22% (USP) active by weight.

The present invention also embraces a method of inhibiting or reducing perspiration by topically applying an effective amount of an antiperspirant composition as described herein to the skin of a human, preferably to the axilla, where such reduction in perspiration is desired by the user. An effective amount is that amount which provides at least a 20% sweat reduction, preferably at least a 40% sweat reduction, when tested in accordance with a standard hot room thermal efficacy protocol, and most preferably that amount which reduces perspiration to a degree that is noticeable by the user. Typically, the amount of antiperspirant composition applied will range from about 0.1 gram to about 1.0 gram per axilla depending on the formulation or such amount as will deliver about 0.01 to about 0.25 gram of antiperspirant active per axilla.

The present invention may be further illustrated by the following examples in which the parts and percentages are by weight. In these examples, the abbreviation ACH' means enhanced efficacy 5/6 basic aluminum chlorohydrate with an Al:Cl ratio of about 1.95 and having an HPLC peak 4 to peak 3 area ratio of at least 0.7 with at least 80% of the aluminum contained in peaks 3 and 4. The ACH' is made by diluting ACH with water to form a solution of about 10% concentration, heating the dilute ACH solution at about 85° C. for about 16 hours, then rapidly concentrating the ACH' by vacuum evaporation (for example, using a falling film evaporator) to a concentration of about 42% USP active and cooling to room temperature. The ACH' must be used shortly after preparation in order to insure that it has the desired high peak 4 to peak 3 ratio.

The abbreviation ZHCG means zirconium hydroxychloride-glycine (Zr:Gly≅1). When referring to this material, the Zr:Cl ratio (e.g., Zr:Cl=0.28) will be indicated in parentheses following the abbreviation. The ZHCG may be prepared by reacting zirconium basic carbonate with an appropriate amount of HCl to achieve the desired Zr:Cl ratio, then adding the appropriate amount of glycine. The aqueous ZHCG used in the examples has a Zr content of about 8% by weight Zr. The abbreviation AZCH means aluminum-zirconium chlorohydrate-gly (standard efficacy), EAZCH means a conventional enhanced efficacy AZCH with high peak 4:3 ratio, and E"AZCH means an enhanced efficacy AZCH of the present invention with a low M:Cl ratio and made with a ZHCG having a low Zr:Cl ratio. "Comp." means comparative example.

EXAMPLE 1

Freshly prepared aqueous ACH' solution is mixed with aqueous ZHCG solution (as defined below) in the appropriate molar ratio to provide the desired Al:Zr ratio along with sufficient HCl, as needed, to provide the desired M:Cl ratio, thus forming aqueous solutions of enhanced efficacy aluminum-zirconium chlorohydrates (about 30–35% USP active) with Al:Zr mole ratios and M:Cl mole ratios as shown in Table 1 below. The various ZHCG solutions used are as follows: $ZHCG^a$ (Zr:Cl=0.26–0.28), $ZHCG^b$ (a blend of about 60 parts $ZHCG^a$ and about 40 parts $ZHCG^d$ (Zr:Cl=1.05–1.10)), and $ZHCG^c$ (Zr:Cl=0.44). A portion of each antiperspirant salt solution is retained for further testing, and the remainder is spray dried to recover the antiperspirant salt as a powder.

TABLE 1

Enhanced Al—Zr Salts With Low M:Cl

| E" AZCH | ZHCG (Zr:Cl) | Al:Zr | M:Cl |
| --- | --- | --- | --- |
| A | a (0.28) | 10 | 0.94 |
| B | a (0.28) | 6.2 | 0.95 |
| C | a (0.26) | 10 | 0.94 |
| D | b (0.28 + 1.10) | 2 | 0.92 |
| E | b (0.26 + 1.05) | 2 | 0.92 |
| F | a (0.28) | 4.6 | 0.96 |
| G | a (0.28) | 7.8 | 1.15 |
| Comp. | c (0.44) | 2.1 | 0.95 |

[1]Aged 1.5 years as aqueous solution (~33% USP)

EXAMPLE 2

The above-described enhanced efficacy salts of Example 1 are tested for thermal efficacy (i.e. hot room sweat reduction) using volunteer panelists in a standard hot room protocol. The test product is applied to one axilla and control product is applied to the other axilla in an AvB comparison. In all cases, the test product comprises vehicle (as described below) plus enhanced efficacy salt (E"AZCH). The control product comprises vehicle plus conventional enhanced efficacy antiperspirant salt (EAZCH), except for the clear gel formulation, which uses a standard efficacy salt (AZCH) because of the instability of EAZCH in aqueous formulations. To counteract this instability, the formulation identified as "Aqueous" below, is freshly prepared with powdered EAZCH just prior to being tested. The formulations tested are set out below and the results are shown in Table 2. The results are reported as the average sweat reduction ("S.R.") gain over the control (i.e. the absolute percentage point increase in sweat reduction over the control).

Aqueous

20% USP AP active
q.s. water

Clear Gel 23.5% AP active
39.8% Water
8.7% Propylene Glycol
10.0% Ethanol
9.7% Dimethicone
8.1% Cyclomethicone (and) Dimethicone copolyol
0.2% Fragrance Roll-On 20.0% AP active
75.1% Cyclomethicone
3.5% Quaternium-18 hectorite
1.0% Propylene carbonate
.4% Fragrance Solid 23.5% AP active
51.9% Cyclomethicone
13.5% Stearyl alcohol
3.0% Hydrogenated castor oil
4.0% Myristyl myristate
1.8% Silica
2.3% Fragrance/Silk Powder

TABLE 2

Thermal Efficacy of Al—Zr Salts With Low M:Cl

| E" AZCH | Vehicle | Control | Avg. S.R. Gain Over Control |
| --- | --- | --- | --- |
| A | Roll-On | EAZCH | 5.8 (p = 0.0001) |
| B | Aqueous[1] | EAZCH | 7.0 (p = 0.004) |
| C | Aqueous | EAZCH | 4.2 (p = 0.025) |
| C | Clear Gel | AZCH | 15.9 (p = 0.0001) |
| C | Clear Gel[2] | AZCH | 13.3 (p = 0.0001) |
| D | Aqueous | EAZCH | 5.9 (p = 0.0001) |
| D | Aqueous | EAZCH | 4.6 (p = 0.002) |
| D | Roll-On | EAZCH | 8.7 (p = 0.0001) |
| E | Aqueous | EAZCH | 4.5 (p = 0.059) |
| E | Solid | EAZCH | 4.0 (p = 0.012) |
| F | Aqueous | EAZCH | 4.3 (p = 0.001) |
| G | Aqueous | EAZCH | 1.7 (N.S.[3]) |
| Comp. | Aqueous | EAZCH | 1.3 (N.S.) |

[1]Aged 1.5 years
[2]Aged 3 months at 45° C.
[3]N.S. = not significant

From the above data, it can be seen that the enhanced antiperspirant salts (E"AZCH) of the present invention (e.g., salts A, B, D, E, and F) are more efficacious than conventional enhanced antiperspirant salts (EAZCH), and by indirect comparison, more efficacious than the salt of the comparative example (Comp.), which is a salt similar to salts D and E, but made with a ZHCG with a higher Zr:Cl ratio (i.e., outside the range of the present invention). It is also shown that the E"AZCH salt (salt B) retains its superior efficacy when stored as a concentrated aqueous solution (in this case, for 1.5 years). Conventional enhanced salts lose their enhanced state in aqueous solution. When formulated as a clear gel, the E"AZCH salt (salt C) is substantially more efficacious than the current commercial clear gel product, which must use a standard efficacy salt, and this salt maintains its high efficacy even after storage of the clear gel at high temperature. Salt G, with a somewhat higher M:Cl ratio of 1.15, is just as efficacious as a conventional enhanced salt and could be an advantageous alternative, particularly in aqueous based formulations.

Reference throughout this application to weight percent of antiperspirant salt is intended to be calculated as anhydrous weight percent in accordance with the new U.S.P. method. This calculation excludes any bound water and glycine. For aluminum-zirconium chlorohydrate, the calculation is as follows:

%AZCH=%Al{26.98y+92.97+17.01[3y+4−(y+1)/z]+35.45(y+1)/z}/26.98y where y=Al/Zr ratio and z=metal/Cl ratio.

For reference purposes, calculation of antiperspirant salt weight percent in accordance with the U.S.P. method compares to the previously used standard industry method as follows: 50% AZCH (std)≅38.5% USP.

What is claimed is:

1. An aluminum-zirconium chlorohydrate having a metal (Al+Zr) to chloride ratio of about 0.9 to about 1.2, wherein said aluminum-zirconium chlorohydrate is made with a zirconium hydroxychloride of the formula $Zr(OH)_{4-b}Cl_b$ wherein b is 2.8 to 4.0 so that the Zr:Cl ratio in said zirconium hydroxychloride is 0.36 to 0.25.

2. The aluminum-zirconium chlorohydrate of claim 1 which is an aluminum-zirconium tetrachlorohydrate.

3. The aluminum-zirconium chiorohydrate of claim 1 which is an aluminum-zirconium octachlorohydrate.

4. The aluminum-zirconium chlorohydrate of claim 1 having the formula $Al_nZr(OH)_{[3n+4-m(n+1)]}(Cl)_{[m(n+1)]}$ wherein n is 2.0 to 10.0 and m is about 0.83 to about 1.11

5. The alumiinum-zirconium chlorohydrate of claim 4 wherein m is about 0.90 to about 1.11.

6. The aluminum-zirconium chlorohydrate of claim 1 wherein b is about 3.2 to about 4.0 so that the Zr:Cl ratio in said zirconium hydroxychloride is about 0.31 to about 0.25.

7. The aluminum-zirconium chlorohydrate of claim 5 wherein b is about 3.2 to about 4.0 so that the Zr:Cl ratio in said zirconium hydroxychloride is about 0.31 to about 0.25.

8. The aluminum-zirconium chlorohydrate of claim 1, 5, 6 or 7 in solid powder form.

9. An aqueous composition comprising water and, dissolved therein, an aluminum-zirconium chlorohydrate according to claim 1, 5, 6 or 7.

10. The aqueous composition of claim 9 comprising about 8% to about 45% (USP) of said aluminum-zirconium chlorohydrate.

11. A composition comprising a liquid polyhydric alcohol and, dissolved therein, an aluminum -zirconium chlorohydrate according to claim 1, 5, 6 or 7.

12. The composition of claim 11 comprising about 8% to about 45% (USP) of said aluminum-zirconium chlorohydrate.

13. A clear antiperspirant gel composition comprising a water-in-oil emulsion having a water phase and an oil phase, wherein the water phase comprises an aqueous composition according to claim 9.

14. A topical antiperspirant composition comprising a dermatologically acceptable carrier and a perspiration reducing effective amount of an aluminum-zirconium chlorohydrate according to claims 1, 5, 6 or 7.

15. The topical antiperspirant composition of claim 14 wherein said carrier is an anhydrous carrier and said aluminum-zirconium chlorohydrate is in solid powder form suspended in said anhydrous carrier.

16. The topical antiperspirant composition of claim 15 wherein said anhydrous carrier comprises a silicone.

17. The topical antiperspirant composition of claim 16 in the form of a liquid, lotion, cream, gel, soft-solid, or solid stick.

18. A method of reducing perspiration from human skin comprising applying to human skin a topical antiperspirant composition according to claim 14.

19. A method of reducing perspiration from human skin comprising applying to human skin an aluminum-zirconium chlorohydrate according to claim 1, 5, 6 or 7.

20. A method of preparing an aluminum-zirconium chlorohydrate of the formula $Al_nZr(OH)_{[3n+4-m(n+1)]}(Cl)_{[m(n+1)]}$ wherein n is 2.0 to 10.0 and m is 0.83 to 1.11, which method comprises mixing in an aqueous solution an aluminum antiperspirant salt with a zirconium hydroxychloride salt of the formula $Zr(OH)_{4-b}Cl_b$ wherein b is 2.8 to 4.0, each salt being present in an amount to provide an Al:Zr molar ratio of 2.0 to 10.0, and, if necessary, adjusting the metal (Al+Zr) to chloride ratio (M:Cl) to 0.9 to 1.2 by inclusion of an appropriate amount of a chloride ion source in the aqueous solution.

21. The method of claim 20 wherein the aluminum antiperspirant salt comprises an aluminum chlorohydrate of the formula $Al_2(OH)_{6-a}Cl_a$ wherein a is about 1 to about 2.

22. The method of claim 21 wherein the chloride ion source, if necessary, comprises HCl or $AlCl_3$.

23. The method of claim 22 wherein b is about 3.2 to about 4.0 in said zirconium hydroxychloride salt.

24. The method of claim 20 or 23 which additionally comprises drying said solution to obtain said aluminum-zirconium chlorohydrate in solid form.

25. A method of preparing an aluminum-zirconium chlorohydrate of the formula $Al_nZr(OH)_{[3n+m(n+1)]}(Cl)_{[m(n+1)]}$ wherein n is 2.0 to 10.0 and m is 0.83 to 1.11, which method comprises dry blending an aluminum antiperspirant salt with a zirconium hydroxychloride salt of the formula $Zr(OH)_{4-b}Cl_b$ wherein b is 2.8 to 4.0, each salt including a sufficient molar amount of Al, Zr and Cl and being present in an amount to provide an Al:Zr molar ratio of 2.0 to 10.0 and a metal (Al+Zr) to chloride ratio (M:Cl) of 0.9 to 1.2.

26. An aluminum-zirconium chlorohydrate having a metal (Al+Zr) to chloride ratio of about 0.9 to about 1.2, wherein said aluminum-zirconium chlorohydrate includes a zirconium hydroxychloride of the formula $Zr(OH)_{4-b}Cl_b$ wherein b is 2.8 to 4.0 so that the Zr:Cl ratio in said zirconium hydroxychloride is 0.36 to 0.25.

* * * * *